United States Patent
Jackson, III (10) Patent No.: US 10,939,925 B2
(45) Date of Patent: *Mar. 9, 2021

(54) ILLUMINATED ENDOSCOPIC PEDICLE PROBE WITH REPLACEABLE TIP

(71) Applicant: OPTICAL SPINE, LLC, Grand Blanc, MI (US)

(72) Inventor: Avery M. Jackson, III, Grand Blanc, MI (US)

(73) Assignee: Avery M. Jackson, III, Grand Blanc, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/528,171

(22) Filed: Jul. 31, 2019

(65) Prior Publication Data

US 2019/0350595 A1 Nov. 21, 2019

Related U.S. Application Data

(63) Continuation of application No. 15/891,534, filed on Feb. 8, 2018, now Pat. No. 10,398,451, which is a (Continued)

(51) Int. Cl.
*A61B 1/00* (2006.01)
*A61B 1/015* (2006.01)
(Continued)

(52) U.S. Cl.
CPC ...... *A61B 17/1604* (2013.01); *A61B 1/00045* (2013.01); *A61B 1/00135* (2013.01);
(Continued)

(58) Field of Classification Search
CPC ............ A61B 17/7032; A61B 17/7074; A61B 17/7076; A61B 17/7082; A61B 17/16;
(Continued)

(56) References Cited

U.S. PATENT DOCUMENTS 5,395,383 A 3/1995 Adams et al.
5,474,588 A 12/1995 Tanaka et al.
(Continued)

FOREIGN PATENT DOCUMENTS

WO 2013172869 A1 11/2013
WO 2015184131 12/2015
WO 2017049288 A1 3/2017

OTHER PUBLICATIONS

Photograph of ACI tapered Reamer model TR-3 by Alberta Custom Instruments Ltd. of Edmonton, Alberta Canada. In use since approximately 1987.

*Primary Examiner* — Timothy J Neal
*Assistant Examiner* — William B Chou
(74) *Attorney, Agent, or Firm* — McNees Wallace & Nurick LLC (57) ABSTRACT

An endoscopic pedicle probe for use during spinal surgery to form a hole in a pedicle for reception of a pedicle screw has an enlarged proximal end for cooperation with the hand of the surgeon and an elongate shaft terminating in a distal tip that may be pushed through the pedicle to form the hole. The tip may be detachable for replacement. An endoscope extends through the shaft and is connected with a monitor to enable the surgeon to visually observe the area being treated. In a preferred form a light means extends through the shaft to illuminate the area being treated, and in a further preferred form a conduit extends through the shaft to convey a fluid to flush the area being treated. In a further embodiment, two endoscopes are associated with the probe.

19 Claims, 13 Drawing Sheets

Related U.S. Application Data continuation of application No. 13/728,987, filed on Dec. 27, 2012, now abandoned.

(60) Provisional application No. 61/647,747, filed on May 16, 2012.

(51) Int. Cl.

| | | |
|---|---|---|
| *A61B 1/04* | (2006.01) | |
| *A61B 1/06* | (2006.01) | |
| *A61B 1/12* | (2006.01) | |
| *A61B 17/16* | (2006.01) | |
| *A61B 17/34* | (2006.01) | |
| *A61B 1/313* | (2006.01) | |
| *A61B 17/70* | (2006.01) | |
| *A61B 17/00* | (2006.01) | |

(52) U.S. Cl.
CPC ............... *A61B 1/015* (2013.01); *A61B 1/04* (2013.01); *A61B 1/06* (2013.01); *A61B 1/3135* (2013.01); *A61B 17/00234* (2013.01); *A61B 17/1655* (2013.01); *A61B 17/3472* (2013.01); *A61B 17/7074* (2013.01); *A61B 1/126* (2013.01); *A61B 17/1615* (2013.01); *A61B 17/1671* (2013.01)

(58) Field of Classification Search
CPC . A61B 17/1615; A61B 17/1617; A61B 17/17; A61B 17/1739; A61B 17/1757; A61B 5/06
See application file for complete search history.

(56) References Cited

U.S. PATENT DOCUMENTS

| | | | |
|---|---|---|---|
| 5,573,537 | A | 11/1996 | Rogozinski |
| 5,609,562 | A | 3/1997 | Kaali |
| 5,685,820 | A | 11/1997 | Riek et al. |
| 6,007,481 | A | 12/1999 | Riek et al. |
| 6,387,043 | B1 | 5/2002 | Yoon |
| 6,425,859 | B1 | 7/2002 | Foley et al. |
| 6,527,704 | B1 | 3/2003 | Chang et al. |
| 6,855,105 | B2 | 2/2005 | Jackson, III |
| 7,207,949 | B2 | 4/2007 | Miles et al. |
| 7,722,530 | B2 | 5/2010 | Davison |
| 8,152,714 | B2 | 4/2012 | Garcia-Bengochea et al. |
| 8,221,397 | B2 | 7/2012 | Bleich et al. |
| 8,255,044 | B2 | 8/2012 | Miles et al. |
| 8,979,767 | B2 | 3/2015 | Bartol et al. |
| 9,084,550 | B1 | 7/2015 | Bartol et al. |
| 10,064,671 | B2 | 9/2018 | Sharkey et al. |
| 2003/0013936 | A1 | 1/2003 | Jackson |
| 2003/0171744 | A1 | 9/2003 | Leung et al. |
| 2005/0090833 | A1 | 4/2005 | DiPoto |
| 2006/0074445 | A1 | 4/2006 | Gerber et al. |
| 2007/0005072 | A1 | 1/2007 | Castillo et al. |
| 2007/0016219 | A1 | 1/2007 | Levine |
| 2007/0135803 | A1 | 6/2007 | Belson |
| 2007/0288026 | A1 | 12/2007 | Shluzas |
| 2008/0086140 | A1 | 4/2008 | Wolf |
| 2008/0183214 | A1 | 7/2008 | Copp et al. |
| 2009/0163901 | A1 | 6/2009 | Fisher et al. |
| 2009/0187194 | A1 | 7/2009 | Hamada |
| 2009/0227851 | A1 | 9/2009 | Radojicic |
| 2010/0087823 | A1 | 4/2010 | Kondrashov |
| 2010/0121153 | A1 | 5/2010 | To |
| 2010/0249644 | A1 | 9/2010 | Miles et al. |
| 2011/0077653 | A1 | 3/2011 | Haddock et al. |
| 2011/0160731 | A1 | 6/2011 | Bleich et al. |
| 2011/0184235 | A1 | 7/2011 | Schostek et al. |
| 2011/0313530 | A1 | 12/2011 | Gharib et al. |
| 2013/0253599 | A1 | 9/2013 | Gorek et al. |
| 2014/0073986 | A1 | 3/2014 | Bartol et al. |
| 2014/0142420 | A1 | 5/2014 | Jackson |
| 2015/0032022 | A1 | 1/2015 | Stone et al. |
| 2015/0045891 | A1 | 2/2015 | Poulos |
| 2015/0080755 | A1 | 3/2015 | Jackson |
| 2015/0230749 | A1 | 8/2015 | Gharib et al. |
| 2015/0342621 | A1 | 12/2015 | Jackson |
| 2017/0238788 | A1 | 8/2017 | Jackson |

ILLUMINATED ENDOSCOPIC PEDICLE PROBE WITH REPLACEABLE TIP

CROSS-REFERENCE TO RELATED APPLICATIONS

This application is a continuation of U.S. patent application Ser. No. 15/891,534, filed Feb. 8, 2018, which claims priority to and the benefit of U.S. patent application Ser. No. 13/728,987, filed Dec. 27, 2012, which claims priority to and the benefit of U.S. Provisional Patent Application No. 61/647,747, filed May 16, 2012, the entire contents of which are incorporated by reference herein.

FIELD

This invention relates generally to surgical instruments. More specifically, the invention relates to a pedicle probe for use in forming holes in a vertebral pedicle in preparation for pedicle screw insertion. According to one feature of the invention, the probe incorporates at least one endoscope to enable the surgeon to see the area being treated. According to another feature, the probe has a light to illuminate the area being treated, and according to a further feature, the probe has a replaceable tip on its distal end. According to a still further feature, the probe has a channel for directing a flushing fluid to the area being treated to maintain a clear field of vision for the endoscopic camera. The probe of the invention may have any one or any combination of these features.

BACKGROUND

It is sometimes necessary to perform surgery on the spine in order to repair trauma, correct a deformity, or alleviate the effects of disease. Spinal fusion or stabilization is one procedure that may be employed to treat these conditions. According to one source, at the present time there are approximately 30 million spine procedures performed globally each year, including approximately 400,000 cervical and lumbar fixations performed in the US.

Spinal fusion may be accomplished by insertion of screws into the pedicle to stabilize a spinal segment. The pedicle is a dense, stem-like structure projecting from the posterior of a vertebra, and there are two pedicles per vertebra that connect to other structures. Since the pedicle is the strongest point of attachment of the spine, significant forces can be applied to the spine without failure of the bone-to-metal connection.

To insert pedicle screws, a long, thin, metal probe is inserted through the pedicle and into the vertebral body, forming a hole for reception of the screw. Conventional pedicle probes may be straight or curved, and comprise an elongate solid metal shaft with an enlarged hand grip on the proximal end. The probe may have a shaped distal end adapted for forming a hole through the pedicle, or a separate awl or reamer may first be used to form a hole through the pedicle, and the probe then inserted into the cancellous bone of the pedicle and into the vertebral body to develop a path for the screw.

A variety of probes are known in the prior art, including the so-called gear shift pedicle probe and the Fox pedicle probe. The gear shift probe has a round head on its proximal end, whereas the Fox probe has a flat disc-shaped head on its proximal end.

Conventional modalities used to approximate or simulate screw placement are indirect, and include fluoroscopic guidance and frameless stereotactic guidance. Approximations of the pedicle and surrounding vital structures are obtained from a CT scan or MRI done prior to surgery.

Proper positioning of a conventional probe depends to an extent upon tactile feel. For instance, advancement of the probe should be smooth and consistent. A sudden plunge suggests breaking out of the pedicle laterally, and an increase in resistance indicates abutment against the pedicle or vertebral body cortex.

These conventional modalities require a steep learning curve, and improper or inaccurate manipulation of the probe and placement of the pedicle screw can result in caudal or medial penetration of the pedicle cortex and dural or neural injury.

With conventional pedicle probes there is no direct way to confirm that the hole was made within the pedicle and that the screw will be placed completely inside the pedicle. Surrounding structures can be injured if a portion of the screw is placed outside of the pedicle. There can be nerve root injury, epidural vessel injury, or spinal fluid leakage caused by a misplaced screw.

Applicant's earlier U.S. Pat. No. 6,855,105, discloses an endoscopic pedicle probe having a camera at its distal end connected with an endoscopic monitor via a fiber optic bundle extending through the probe to provide the surgeon with a view of the area being treated, thus overcoming many of the shortcomings of conventional pedicle probes.

Notwithstanding the advantages of applicant's earlier pedicle probe, illumination of the area being treated would greatly enhance use of the probe. Currently, there are no pedicle probes having any means to illuminate the pedicle.

Additionally, the distal tip of the probe can become worn or damaged during use, rendering the whole instrument unusable or reducing its usefulness. Further, in some instances a tip having different characteristics may be desired. A replaceable tip enables this to be achieved without having to replace the entire instrument. Further, body fluids and debris can accumulate at the area being treated, blocking or degrading the view provided by the endoscope. It would be desirable to have a means to flush these fluids and debris away from the area being treated to maintain a clear field of view for the endoscope camera.

Accordingly, there is need for a system and method for insertion of pedicle screws which eliminates the guesswork and error-prone modalities of the prior art. In particular, there is need for a system which provides the surgeon with direct visual confirmation during the surgical procedure that the pedicle probe is in the right position for forming a hole for proper placement of the pedicle screw. Further, there is need for a pedicle probe having a removable distal tip that can be replaced when necessary or desired. Still further, there is need for a pedicle probe having means for illuminating the area being treated. Additionally, there is need for a pedicle probe having means for directing a fluid to the area being treated to remove body fluids and debris that might otherwise obscure the area.

SUMMARY

The present invention comprises a pedicle probe having means associated with it to enable the surgeon to directly confirm the location of the probe during a surgical procedure. More specifically, the invention comprises a pedicle probe which provides the surgeon with a visual indication during a surgical procedure of the position of the probe relative to the pedicle and surrounding structure, and which, in accordance with one aspect of the invention, has means to illuminate the pedicle. In accordance with another aspect of the invention, the distal tip of the probe is replaceable and may be disposable. In a further aspect of the invention, the probe has means associated with it to flush the area being treated to wash away body fluids and debris that would otherwise obscure the field of vision.

In particular, the probe of the invention is an endoscopic probe having an elongate shaft with a reduced diameter tip on its distal end. A camera at the distal end is connected with an endoscopic monitor via a fiber optic bundle extending through the shaft, and depending upon the positioning of the camera and the lens employed, the probe of the invention affords the surgeon direct views of the area being treated, ranging from 0° to 90° relative to the longitudinal axis of the probe shaft, depending upon the positioning of the endoscope camera.

In a preferred embodiment, a light is associated with the probe for illuminating the area being treated.

In another preferred embodiment, the distal tip can be threaded or otherwise securely removably attached to the forward or distal end of the shaft so that the tip can be replaced when worn or damaged or when a tip having different characteristics is desired.

In a further preferred embodiment, means is provided on the probe for flushing the area being treated with a fluid, such as, e.g. saline, to remove body fluids and debris that might otherwise obscure the view.

In one example of the invention, a Fox probe is modified to have a hollow shaft and a small endoscope is placed in the hollow shaft, with a camera positioned at the distal end and connected via a fiber optic bundle with an endoscopic monitor to afford either a 0°, a 45°, or a 90° view, depending upon the lens employed and the positioning of the camera.

The endoscopic pedicle probe of the invention puts the surgeon "in the pedicle" with the use of endoscopy. The positioning of the probe can be directly and accurately determined during surgery, and there is no question as to whether the screw will be too medial, lateral, cranial, caudal, or deep. The surgeon will know if the wall of the pedicle has been breached, and to what extent. He or she can then decide to use the planned trajectory even if there is a small breach of the pedicle wall. The probe of the invention provides the surgeon with knowledge of how much of an intrusion exists, and he or she can ascertain if critical structures will be in danger from screw placement. The surgeon can also avoid parallax that may cause errors when using fluoroscopic guidance.

Further, a probe must be used in any event to perform spinal fusions, and the probe of the invention will not represent an additional instrument needed for pedicle screw placement. Accordingly, there will be no additional costs or equipment needed to perform the standard spinal fusion.

The probe of the invention can be utilized in the cervical spine for lateral mass screw placement, pedicle screw placement, or trans-articular screw placement. It can be used in the thoracic, lumbar, and sacral spine for pedicle screw placement and trans-laminar screw placement, and can be used in standard open spine fusion or in minimally invasive percutaneous spine fusion.

BRIEF DESCRIPTION OF THE DRAWINGS

The foregoing as well as other objects and advantages of the invention will become apparent from the following detailed description when considered in conjunction with the accompanying drawings, wherein like reference characters designate like parts throughout the several views, and wherein.

DETAILED DESCRIPTION

Figure 1:
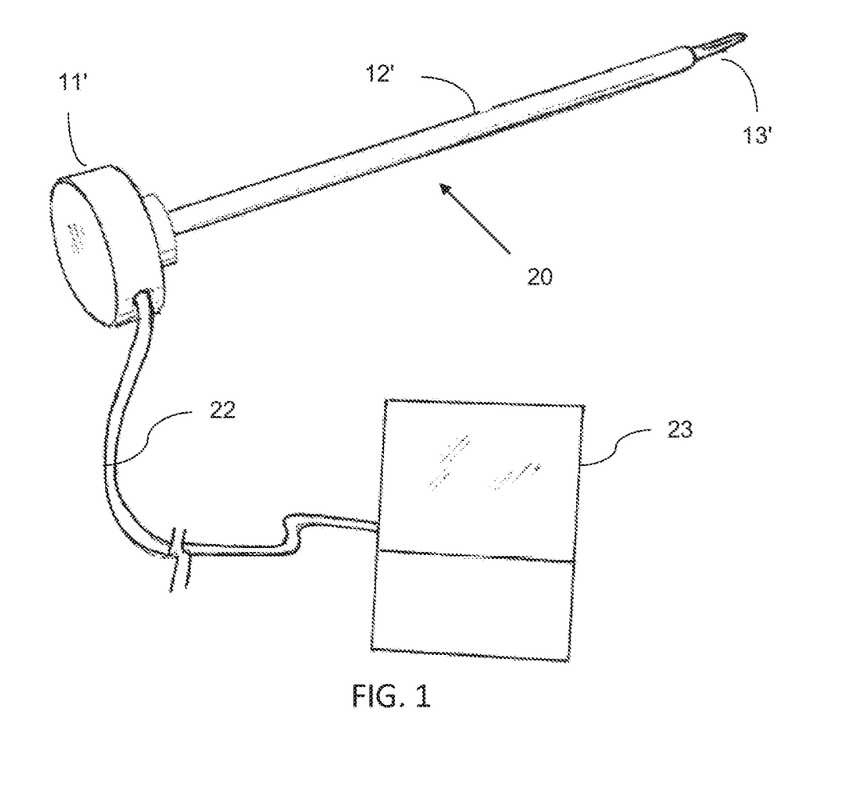
FIG. 1 is a somewhat schematic perspective view of an endoscopic pedicle probe according to the invention, in combination with an endoscopy monitor.
Figure 2:
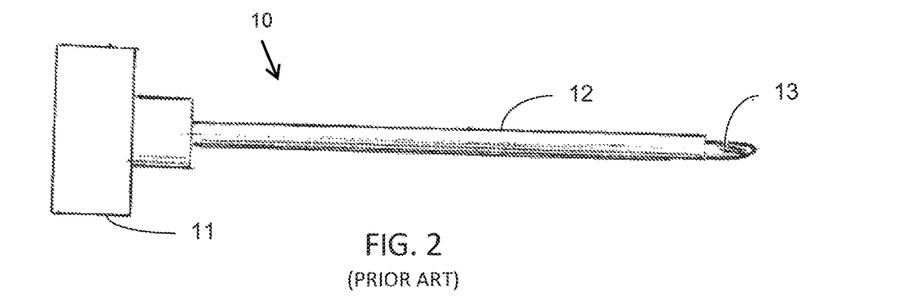
FIG. 2 is a side view in elevation of a conventional pedicle probe on which the present invention can be based.
Figure 3:
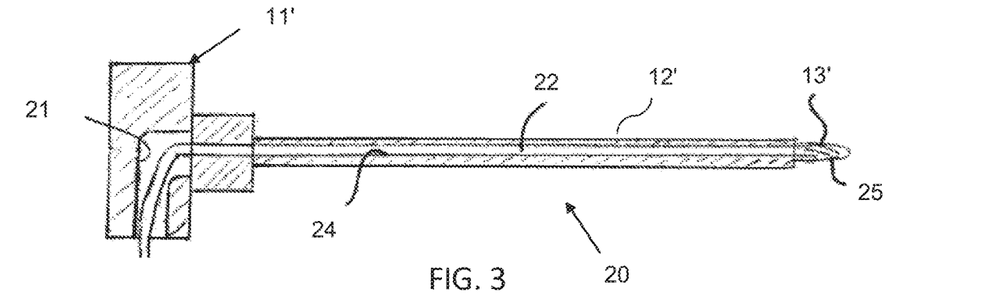
FIG. 3 is a longitudinal sectional view of a first embodiment of endoscopic pedicle probe according to the invention.

Referring more specifically to the drawings, a conventional Fox pedicle probe is depicted at 10 in FIG. 2. The probe has a disc-shaped head 11 on its proximal end that is about two inches in diameter, and a solid metal shaft 12 projecting from the center of one side thereof. A reduced diameter tip 13 on the distal end of the shaft is configured to act as a reamer, i.e., it may have a fluted configuration as found on drill bits. In use, a surgeon places the disc-shaped head 11 in the palm of his or her hand, with the shaft extending forwardly. The tip is then pushed against the pedicle while the probe is being rotated back and forth about the longitudinal axis of the shaft to form a hole in the pedicle for reception of a pedicle screw. See, for example, FIGS. 9-14.

In the specific embodiment illustrated and described herein, the pedicle probe 20 of the invention, as shown in FIGS. 1 and 3-15, is based on the Fox pedicle probe of FIG. 2. However, it should be understood that the probe 20 could be based on other commercially available probes, or could embody a completely new design. The disc-shaped head 11' of the probe 20 has an opening 21 formed in it for receipt of a fiber optic cable or endoscope 22, which is connected with a suitable conventional monitor 23. Similarly, the shaft 12' has a bore 24 formed through its length for receipt of the fiber optic cable or endoscope 22, which terminates in the tip 13' at a lens 25. As in conventional pedicle probes, such as the Fox pedicle probe, the tip 13' is adapted to penetrate the hard bony tissue of a vertebral pedicle to form a hole for reception of a pedicle screw.

As shown in the drawings, the tip has a substantially uniform diameter through a portion of its length, and terminates in a sharpened point. The diameter of the tip is approximately the same as, or slightly smaller than, the diameter of a pedicle screw to be inserted in the hole formed with the probe, and will form an elongate hole having a uniform diameter for secure engagement with a screw inserted in the hole. The tip has a hardness and configuration to act as a reamer, and preferably has a fluted configuration as incorporated, for example, in a conventional Fox pedicle probe, to facilitate penetration of the probe through the hard bony tissue.

Figure 4:
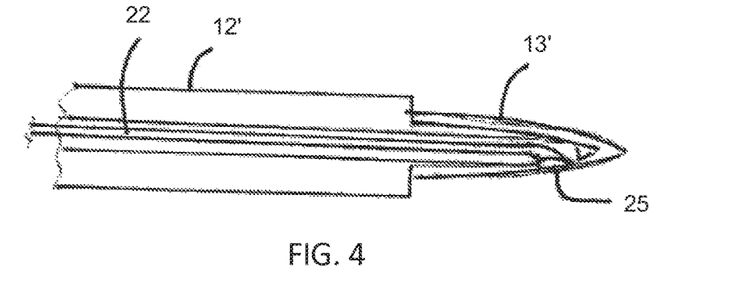
FIG. 4 is an enlarged, fragmentary, longitudinal sectional view of the distal end of the endoscopic pedicle probe of FIG. 3, depicting a 90° lens orientation.
Figure 5:
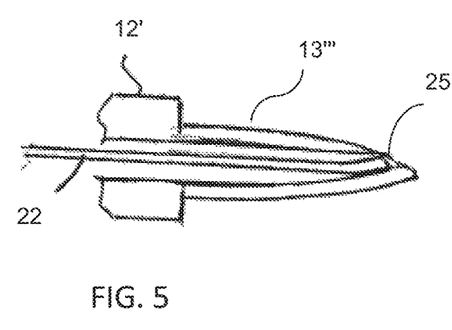
FIG. 5 is a view similar to FIG. 4, but showing a 45° lens orientation.
Figure 6:
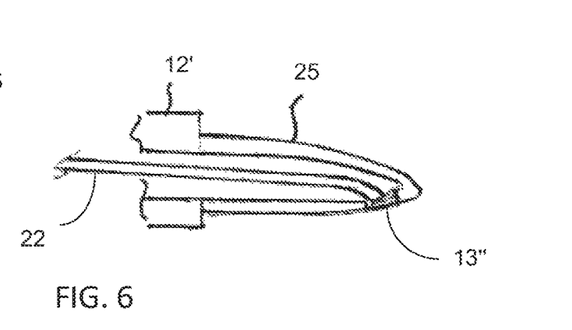
FIG. 6 is a view similar to FIG. 5, but showing a 0° lens orientation.

As shown in FIGS. 4, 5, and 6, respectively, the tip 13' or 13" or 13'" can be configured to position the lens 25 for providing a 90° view (FIG. 4), or a 45° forward view (FIG. 5), or a 0° view straight ahead (FIG. 6). Thus, by selection of an appropriate probe, or by appropriate manipulation of a probe, the surgeon can obtain a direct visual indication of the exact position of the probe in the pedicle and of the pedicle itself and surrounding structure. As depicted in these FIGS., the lens is placed rearwardly of the distal point of the end to protect it when the probe is pressed against and pushed through hard bony tissue. An obturator, not shown, may be provided to close the opening through the side of the tip and protect the lens 25.

Figure 15:
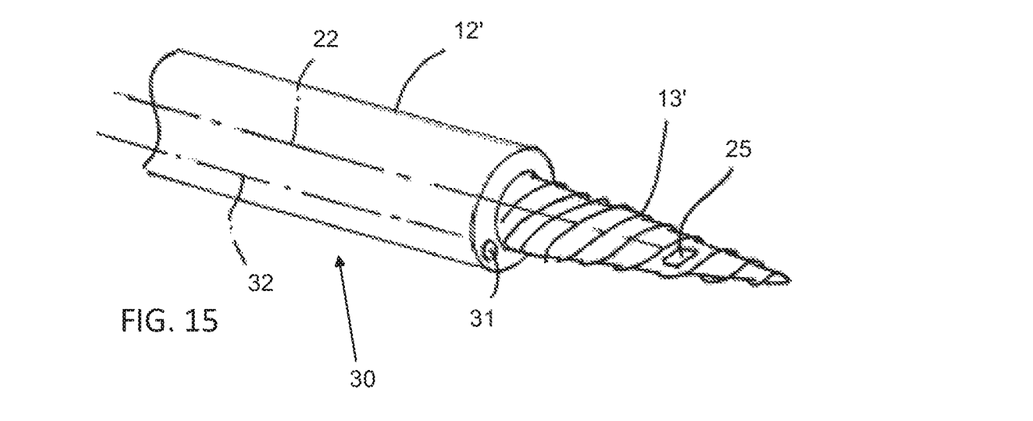
FIG. 15 is an enlarged fragmentary isometric view of the distal end of one embodiment of pedicle probe according to the invention, showing light means for illuminating the pedicle.

A second embodiment of probe 30 is shown in FIG. 15. In this modification, a suitable light 31 is placed at the distal end of the shaft 12' adjacent the base end of the tip 13'. The light 31 is connected via fiber optics 32 or other suitable means extended through the shaft 12' and connected with a suitable light source (not shown) external of the probe, and may be positioned to face axially forwardly of the shaft, as shown in FIG. 15, or at an angle to the longitudinal axis of the probe. In use, the light illuminates the pedicle in the area being treated to provide the surgeon with enhanced visibility of the area as observed through the lens 25 of the endoscope 22.

Figure 16:
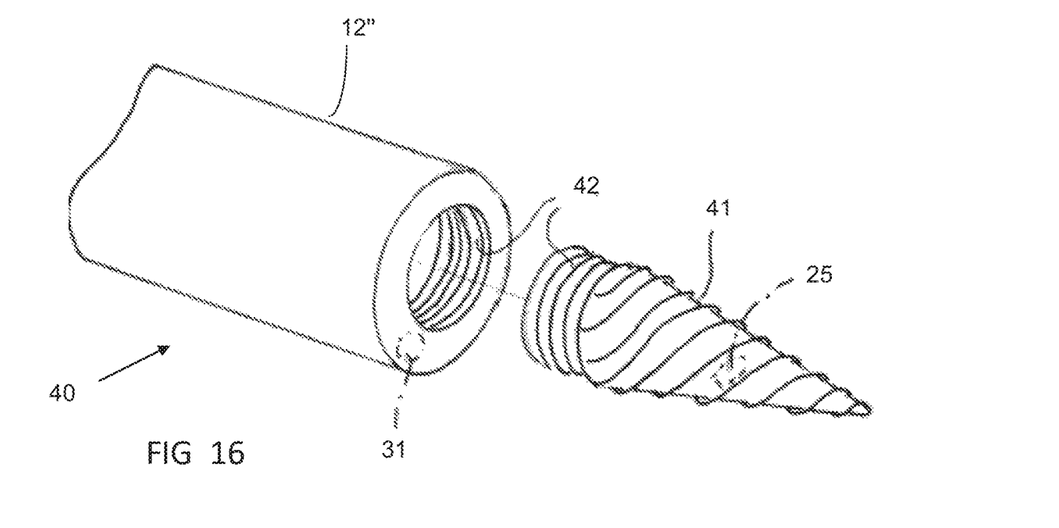
FIG. 16 is an enlarged fragmentary isometric view of the distal end of one embodiment of pedicle probe according to the invention, showing a removable tip.
Figure 17:
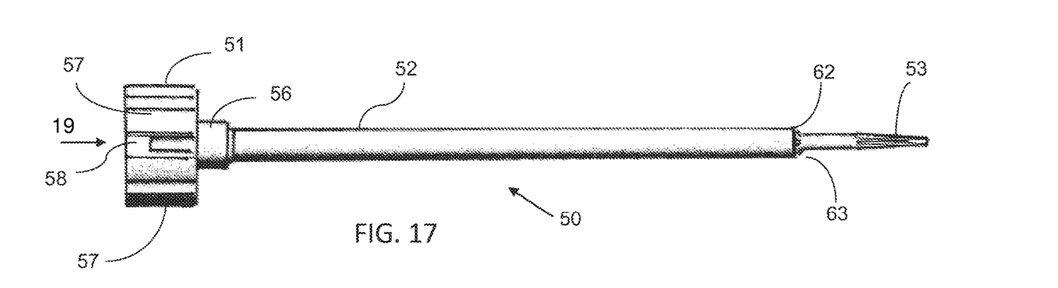
FIG. 17 is a side view in elevation of another embodiment of pedicle probe according to the invention.
Figure 18:
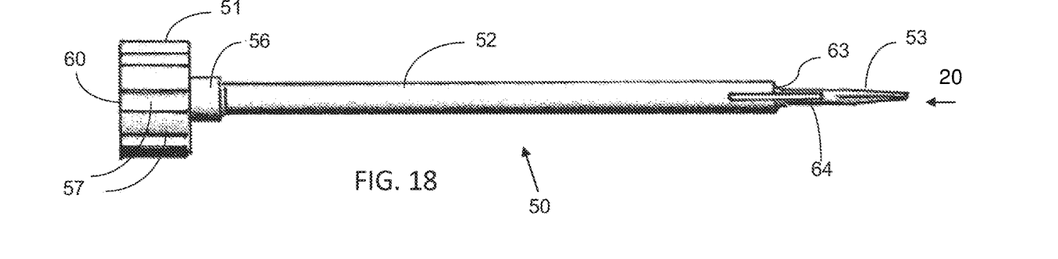
FIG. 18 is a side view in elevation of the probe of FIG. 17, taken at 90 degrees to the view in FIG. 17.
Figure 19:
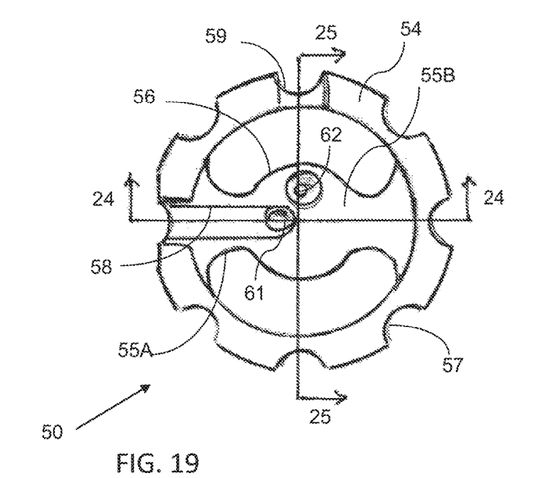
FIG. 19 is an end view of the probe of FIGS. 17 and 18, taken in the direction of the arrow 19 in FIG. 17.
Figure 20:
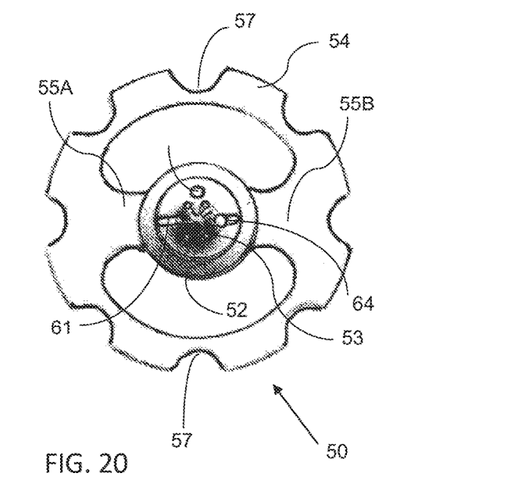
FIG. 20 is an end view of the probe of FIGS. 17 and 18, taken in the direction of the arrow 20 in FIG. 18.
Figure 21:
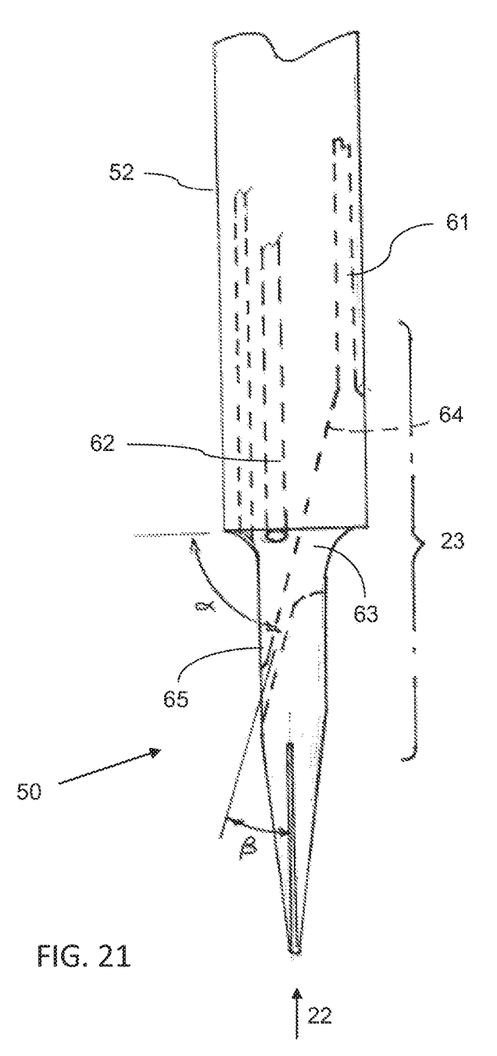
FIG. 21 is an enlarged fragmentary view in elevation of the distal end of the shaft and the tip on the distal end in the embodiment of the probe shown in FIGS. 17-20.
Figure 22:
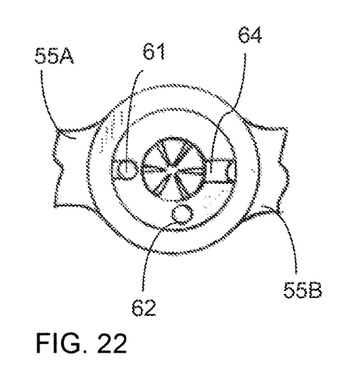
FIG. 22 is a further enlarged fragmentary end view of the probe of FIG. 21, taken in the direction of the arrow 22 in FIG. 21.
Figure 23:
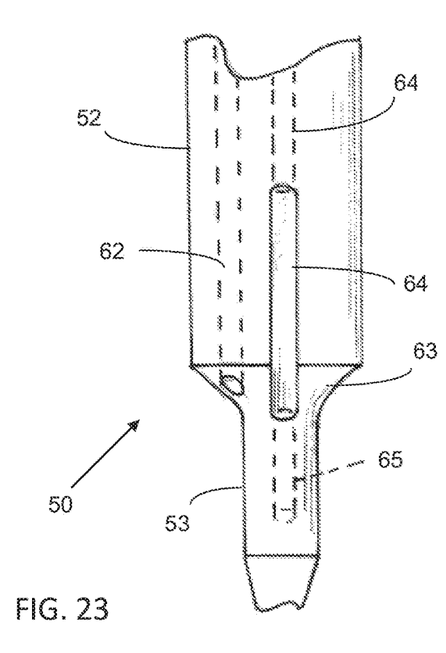
FIG. 23 is a slightly enlarged fragmentary side view in elevation of the area indicated generally by the bracket 23 in FIG. 21.
Figure 24:
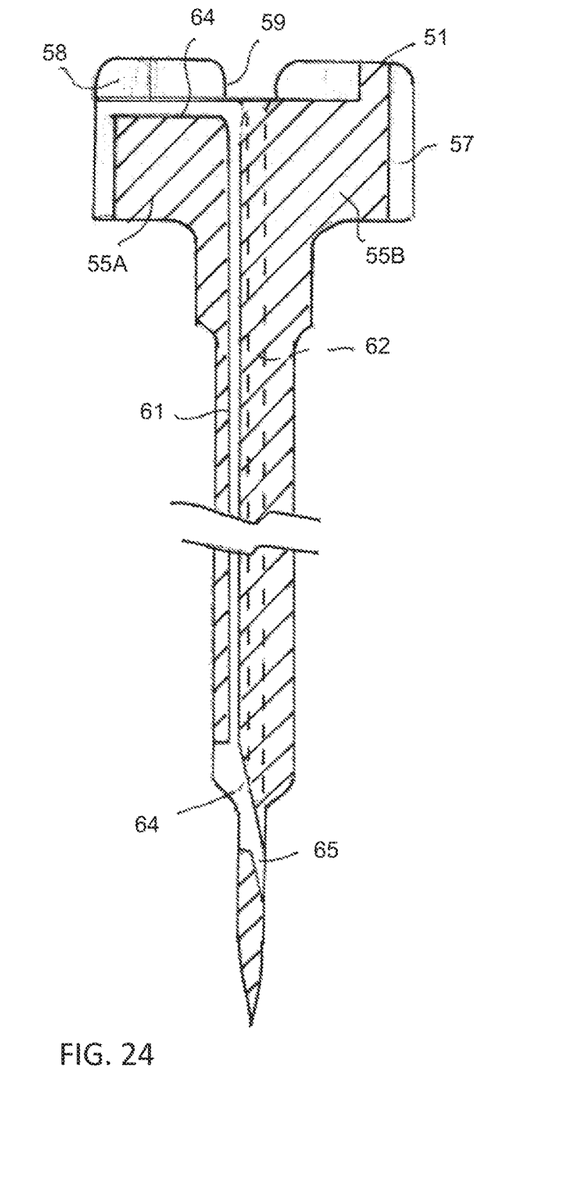
FIG. 24 is a sectional view taken along line 24-24 in FIG. 19.
Figure 25:
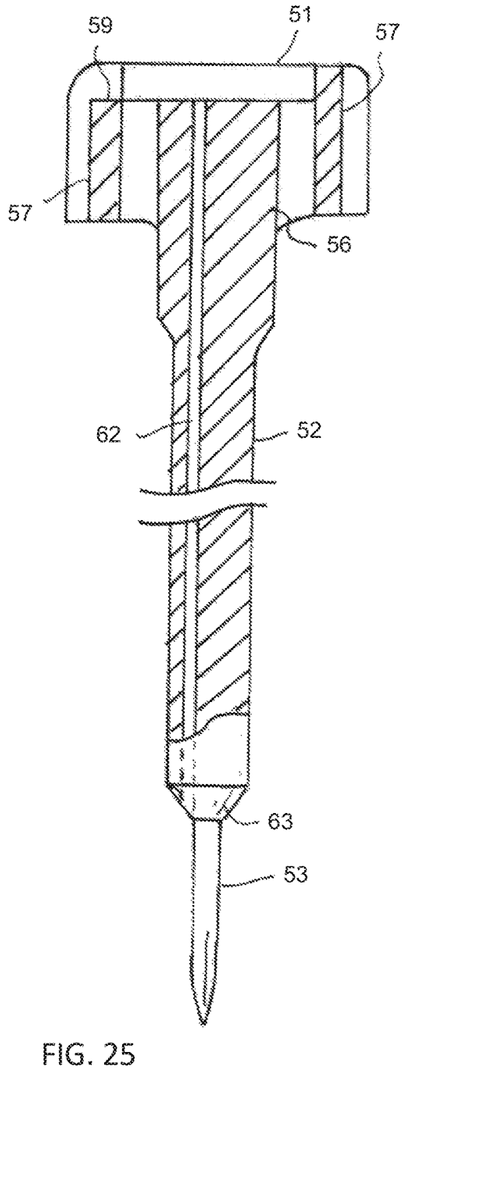
FIG. 25 is a sectional view taken along line 25-25 in FIG. 19.

FIG. 16 depicts a third embodiment 40 of a pedicle probe in which the tip 41 is removable. In the example shown, the removable tip has a threaded connection 42 with the shaft 12", but other means (not shown) of securely removably attaching the tip 41 to the shaft could be utilized. The removable tip may be made of any suitable material, including carbon fiber, and enables tips with different designs to be used on the probe and also enables the tip to be replaced if it becomes worn or damaged during use, thereby avoiding the necessity of having to replace or dispose of the entire probe. The removable tip may be used without either the endoscope of FIGS. 3-6 or the light of FIG. 15, or it may be used in combination with either or both the endoscope and light, shown as optional features in broken lines at 25 and 31 in FIG. 16.

Figure 7:
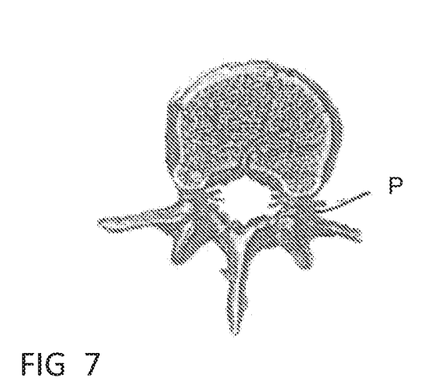
FIG. 7 is an axial view of a pedicle.
Figure 8:
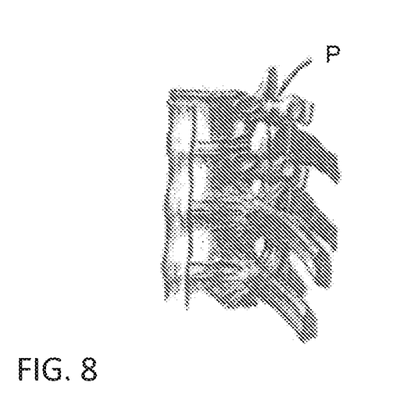
FIG. 8 is a sagittal view of a pedicle.
Figure 9:
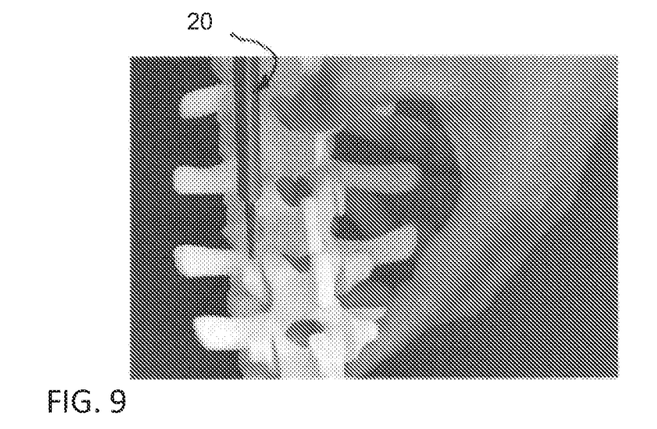
FIGS. 9 and 10 are fragmentary perspective views depicting how a pedicle probe is used to form a hole in a pedicle.
Figure 10:
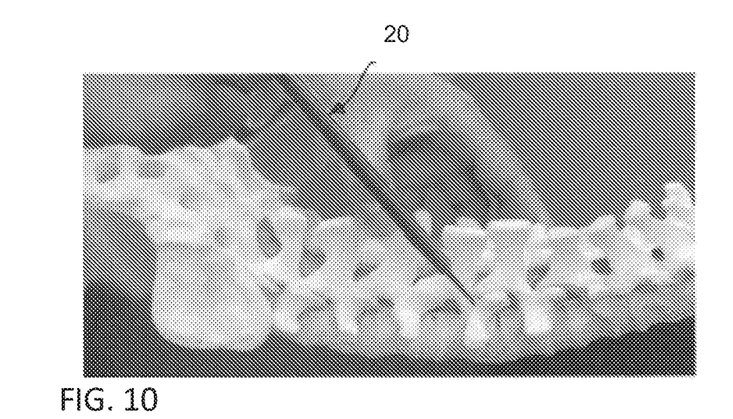
Figure 11:
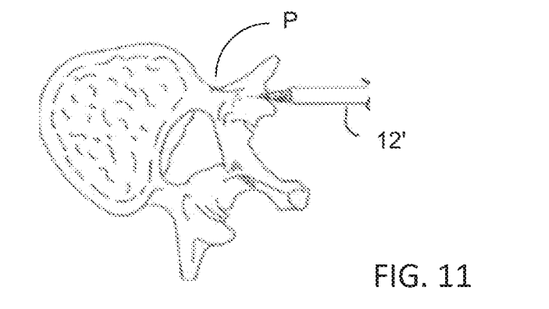
FIGS. 11-14 are somewhat schematic views depicting the progressive steps in forming a hole in the pedicle using the pedicle probe.
Figure 12:
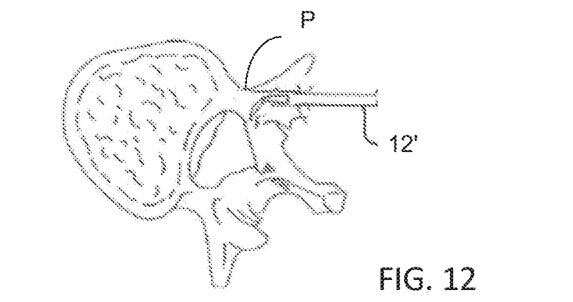
Figure 13:
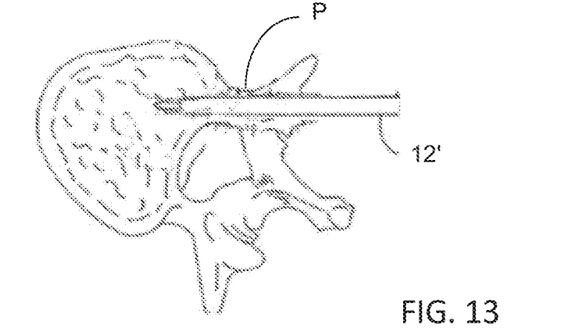
Figure 14:
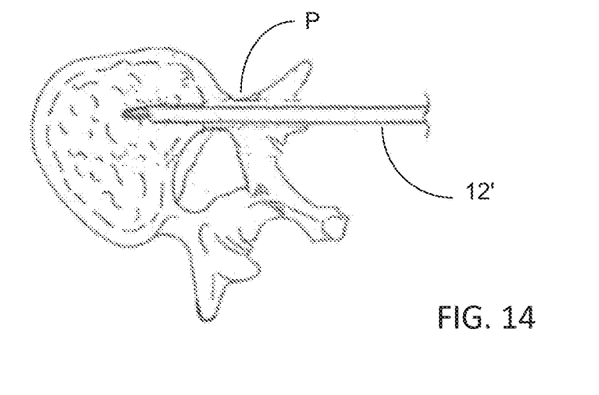

FIGS. 7 and 8 are axial and sagittal views, respectively, of a pedicle P, and FIGS. 9-14 are schematic illustrations of how a probe 20 might be used to form a hole in the pedicle. Thus, and as seen especially in FIGS. 10-14, the probe is pushed through the pedicle to form a hole for reception of a pedicle screw (not shown). Depending upon the structure of the tip 13', the probe also may be rotated back and forth to assist in forming the hole. Great care must be exercised to ensure that the probe stays within the pedicle and does not break through the wall, or does not go too deep.

A fourth embodiment 50 of the pedicle probe according to the invention is shown in FIGS. 17-25. The probe 50 has an enlarged generally disc-shaped head 51 on its proximal end for grasping by the surgeon as in the previous embodiments, an elongate reduced diameter shaft 52 projecting from the center of one side of the head, and a further reduced diameter tip 53 extending coaxially from the distal end of the shaft. The head comprises a circumferential rim 54 connected to the proximal end of the shaft 52 by at least two spokes 55A and 55B that join the rim with a hub 56 on the proximal end of the shaft. The outer surface of the rim is longitudinally fluted at 57, and two circumferentially spaced recesses 58 and 59 are formed in the upwardly facing proximal end surface 60 of the rim. As used herein, "upwardly facing" refers to the orientation when the probe is in its operative position during use. In the particular construction shown, the recesses are in alignment with respective flutes 57 and are circumferentially spaced apart 90 degrees. Two bores 61 and 62 are formed longitudinally through the hub and shaft in positions oriented respectively on a radius extending through a respective recess 58 or 59. One of the bores 62 exits the distal end of the shaft in an axially forwardly facing shoulder 63 between the base end of the tip and the adjacent end of the shaft. The other bore 61 ends in a slot 64 formed in the side of the shaft at its distal end and extending angularly at an angle β of 16 degrees relative to the longitudinal axis of the shaft into the base end of the tip. A bore 65 extends from the slot and diagonally through the tip to exit an opposite side of the tip, providing a view extending over an angle α of 74 degrees.

Figure 26:
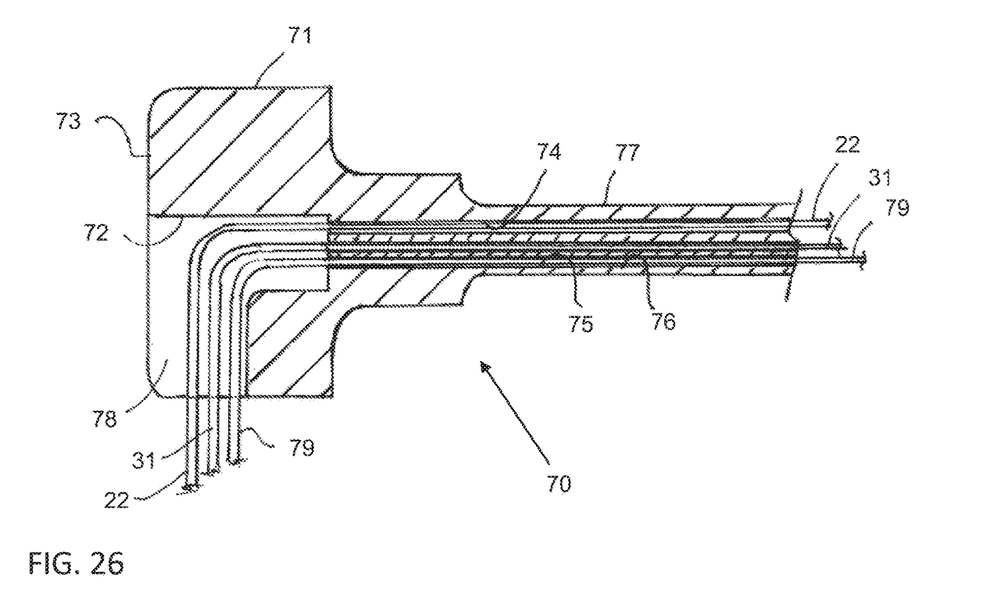
FIG. 26 is a fragmentary longitudinal sectional view of another embodiment of a pedicle probe according to the invention.
Figure 27:
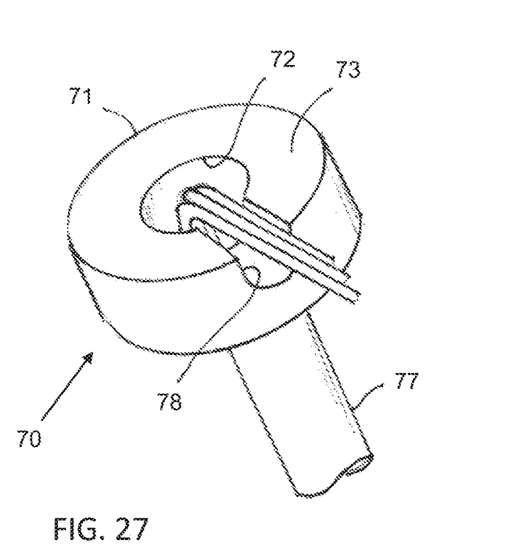
FIG. 27 is a fragmentary top isometric view of the probe of FIG. 26.
Figure 28:
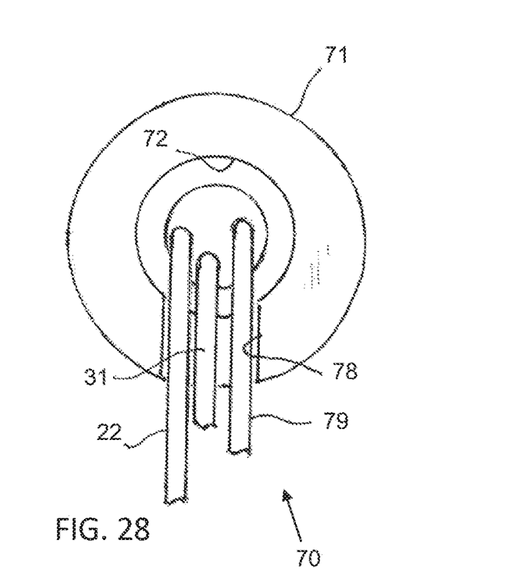
FIG. 28 is an end view in elevation of the probe of FIG. 26, looking from the left hand side of FIG. 26.
Figure 29:
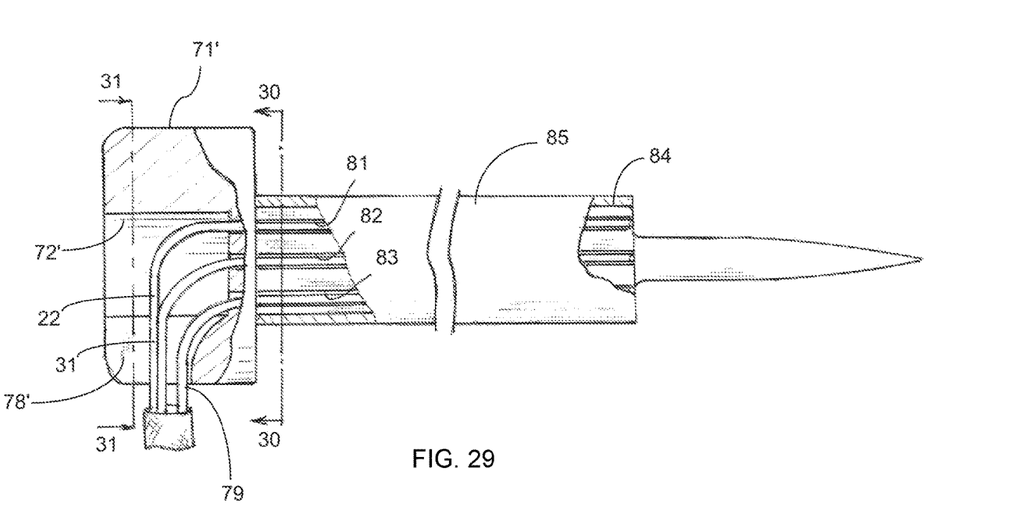
FIG. 29 is a side view, shown partially in section and partially in elevation, of a further modified probe according to the invention, wherein channels are formed in the outer surface of the probe shaft and feeds for the light, camera and flushing liquid are placed in these channels, with a surrounding sleeve placed over the shaft to secure the parts in place.
Figure 30:
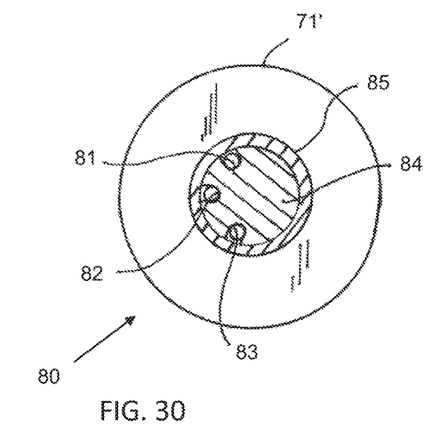
FIG. 30 is a transverse sectional view taken along long line 30-30 in FIG. 29.
Figure 31:
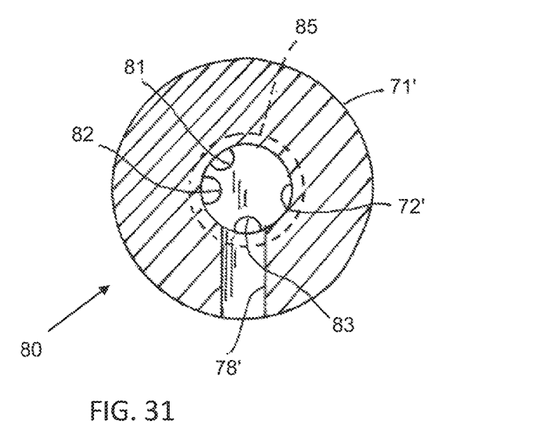
FIG. 31 is a transverse sectional view taken along long line 31-31 in FIG. 29.
Figure 32:
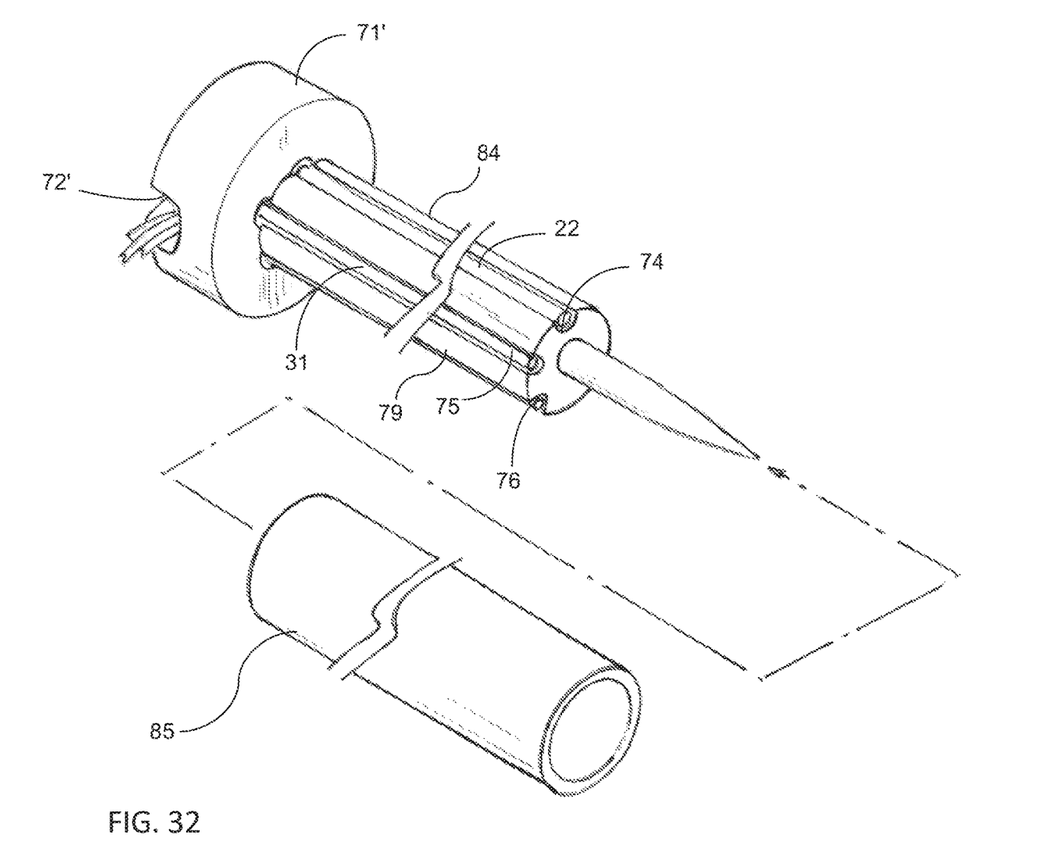
FIG. 32 is an exploded isometric view, with portions broken away, of the probe and sleeve of FIGS. 29-31.

A fifth embodiment 70 of the pedicle probe according to the invention is shown in FIGS. 26-28. In this embodiment, the proximal end or head 71 of the probe has a central opening 72 extending inwardly from its axially upwardly facing surface 73, and a plurality of bores 74, 75, and 76 extend longitudinally through the shaft 77 from the base of the opening. A radial notch 78 in the axially upwardly facing surface connects the central opening with the outer circumference of the head. An endoscope 22, light 31, and conduit 79 for conveying a flushing fluid to the distal end of the probe to remove body fluids and debris from the area being worked on extend through the notch 78 and through the bores 74, 75, and 76, respectively. Although not shown in FIGS. 26-28, the bores 74, 75 and 76 could exit through the shoulder between the base end of the tip and the distal end of the shaft (see, e.g. shoulder 63 in FIGS. 24 and 25), or the endoscope bore could terminate in a slot such as slot 64 seen in FIGS. 21-23. Also not shown in FIGS. 26-28, the tip could be integrally formed with the shaft as seen in FIGS. 17-25 or it could be detachable as seen in FIG. 16.

A sixth embodiment 80 of the pedicle probe according to the invention is shown in FIGS. 29-32. In this form of the invention, rather than extend bores longitudinally through the body of the shaft for containing the endoscope, light, and conduit for the flushing fluid, longitudinally extending channels 81, 82, and 83 are formed in the outer surface of the shaft 84, and a cylindrical sleeve 85 is positioned in snug relationship over the shaft in enclosing relationship to the channels and the endoscope 22, light 31, and conduit 79 held therein. As in the previous embodiments, the tip may be integral with the shaft or detachable. Similarly to the embodiment shown in FIGS. 26-28, the head 71' has a central opening 72' and the endoscope 22, light 31, and flushing conduit 79 are fed through a notch 78' in the end surface of the head.

Figure 33:
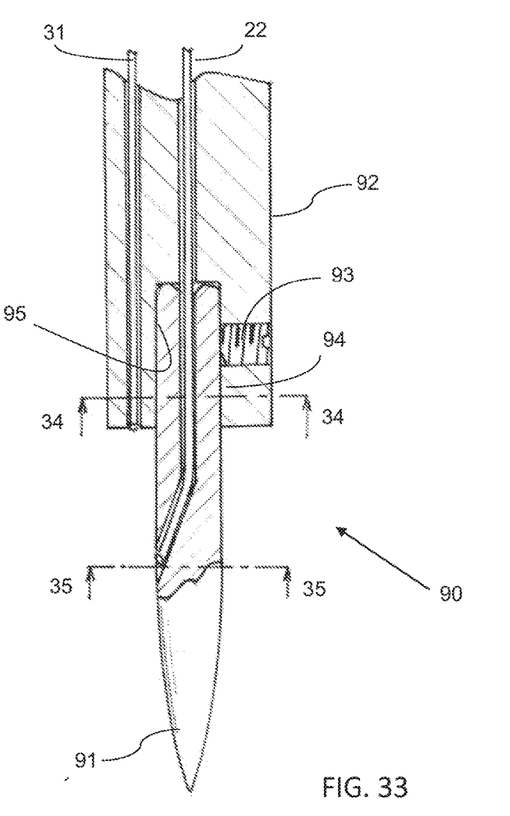
FIG. 33 is a fragmentary enlarged sectional view of the distal end of a further embodiment of the invention wherein a removable tip is held in place by a set screw and is aligned in proper position by a keyway.
Figure 34:
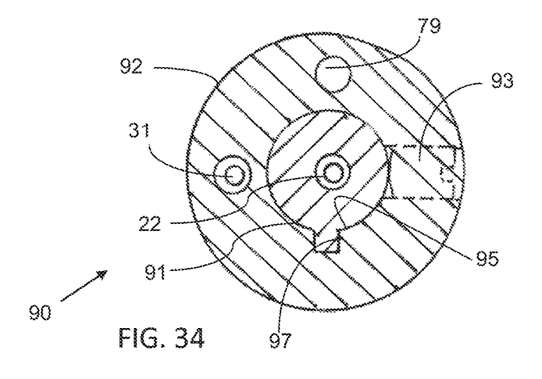
FIG. 34 is a transverse view in section taken along line 34-34 in FIG. 33.
Figure 35:
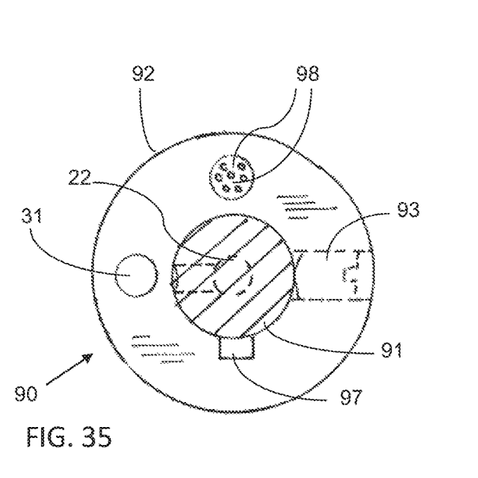
FIG. 35 is a transverse view in section taken along line 35-35 in FIG. 33.

A seventh embodiment 90 of the pedicle probe according to the invention is shown in FIGS. 33-35. In this form of the invention, the tip 91 is detachably secured to the distal end of the shaft 92 by a set screw 93 extended through the side of the shaft and into engagement with the base end 94 of the tip, which is inserted into an axial bore 95 in the distal end of the shaft. Proper rotational positioning of the tip relative to the shaft is achieved by a keyway formed by an axially extending groove or slot 96 in the interior surface of bore 95 and a complementally shaped key 97 on the exterior of the base end 94 of the tip. The tip may be readily detached from the shaft by loosening the set screw and may be used with any of the previous forms of the invention. An endoscope 22 and/or a light 31 and/or a conduit 79 for flushing fluid, all shown in FIGS. 33-35, may be used in combination with the detachable tip, or the detachable tip may be used without any of these. As seen in FIG. 35, the outlet for the flushing fluid may have numerous small orifices 98 to provide a "soft" flow of flushing fluid against the area being treated.

Figure 36:
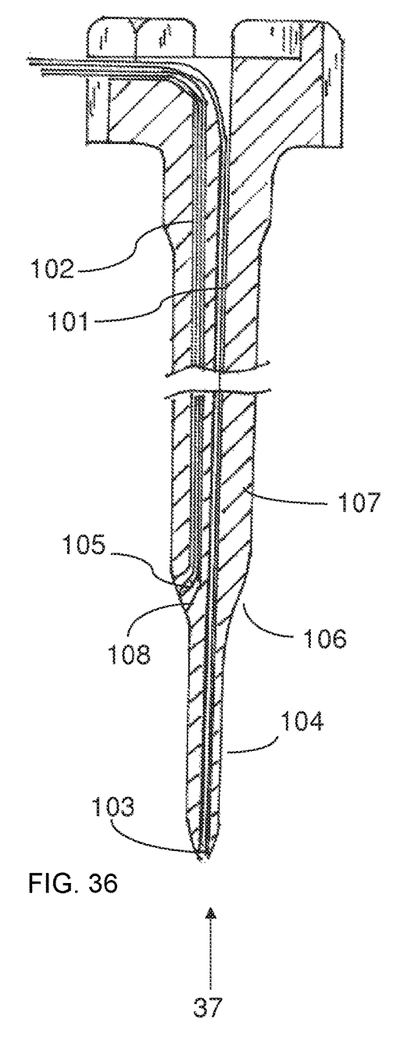
FIG. 36 is a longitudinal sectional view of a further embodiment of the invention, taken along line 36-36 in FIG. 37, wherein two endoscopes are associated with the probe, and a light means and saline flush means are provided for illuminating the area being treated and for flushing away debris to maintain a clear field of view.
Figure 37:
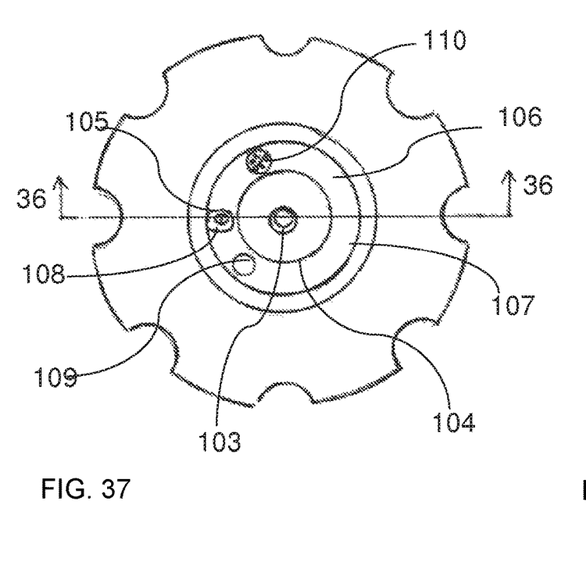
FIG. 37 is an enlarged end view looking in the direction of the arrow 37 in FIG. 36.

An eighth embodiment 100 of the probe according to the invention is shown in FIGS. 36 and 37. In this embodiment, a first endoscope 101 and a second endoscope 102 are provided in the probe. The first endoscope 101 has a first camera 103 positioned at the distal end of the tip 104 in a zero degree forwardly facing orientation. The second endoscope 102 has a second camera 105 positioned at the distal end 106 of the probe shaft 107 and oriented in a camera window slot 108 to provide about a 70° view looking at the side of the pedicle wall. A bright fiber optic light source 109 is positioned at the distal end of the probe shaft adjacent the window for the camera 105. The light illuminates the pedicle and surrounding bony structures which will give visualization within the cancellous portion of the pedicle. A saline rinse port 110 also preferably is provided at the distal end of the probe shaft to rinse away debris during use of the probe to keep the field of vision clear.

One example of a suitable endoscopic camera for use in the probe of the invention is the 1.2 mm micro camera available from Medigus, Ltd. of Omer, Israel. This camera has a diameter of only 1.2 mm and a length of only 5 mm. It has high quality 100 degree FOV optics and a shielded camera cable with a metal connector as well as a video processor.

In a typical example of a probe made in accordance with the invention, the shaft can have a length of about 28 cm and a diameter of from about 6 mm to about 12 mm; the tip can have a length of about 40 mm and a diameter of from 4 mm to about 5 mm; and the endoscope 22, light 32, and conduit 79 for flushing fluid each can have a diameter of from about 1 mm to about 2 mm. In those embodiments wherein the camera for the endoscope is located adjacent the proximal end of the tip, it can be placed along the tip a distance spaced approximately 6 mm to 8 mm from where the tip is joined to the end of the shaft, and preferably is oriented at an angle of 45 degrees to 90 degrees relative to the longitudinal axis of the tip. It should be noted that these are exemplary dimensions only and the probe and its components could have other dimensions as necessary or desirable.

The endoscopic probe of the invention provides the surgeon with an illuminated, direct visual indication of the exact location of the probe and provides for flushing body fluids and debris away from the area being treated, whereby the hole can be formed with accuracy and precision.

While particular embodiments of the invention have been illustrated and described in detail herein, it should be understood that various changes and modifications may be made to the invention without departing from the spirit and intent of the invention as defined by the scope of the appended claims.

What is claimed is:
1. A probe, comprising:
  an enlarged proximal end for cooperation with the hand of a surgeon using the probe to aid in controlling the probe;
  an elongate shaft having a longitudinal axis and extending from the enlarged proximal end to a distal end;
  a reduced diameter tip at the distal end of the shaft, the tip having a sharpened distal point having a hardness and configuration adapted to be pushed through a vertebral pedicle to form a hole for reception of a pedicle screw;
  a first bore extending longitudinally through the shaft, and a first endoscope associated with the first bore, the first endoscope including a camera and placed within the first bore in the shaft rearward of the distal point of the tip and being connected with an endoscopic monitor to provide the surgeon with a first direct view of an area being treated; and a second bore extending longitudinally through the shaft, and a light associated with the second bore, the light including an optical connector placed within the second bore in the shaft rearward of the distal point of the tip and being connected with a light source to illuminate the area being treated.

2. The probe of claim 1, wherein the optical connector is fiber optic.

3. The probe of claim 1, further including a third bore extending longitudinally through the shaft, and a second endoscope associated with the second bore, the second endoscope including a camera positioned at the distal end of the shaft and being connected with an endoscopic monitor to provide the surgeon with a second direct view of the area being treated.

4. The probe of claim 3, wherein the first endoscope and the second endoscope are connected with the endoscopic monitor.

5. The probe of claim 1, further including a fourth bore extending longitudinally through the shaft, and a conduit extending through the fourth bore for conveying a fluid to the area being treated to flush away from the area being treated body fluid and debris that would otherwise obscure the area being treated.

6. The probe of claim 1, wherein the first bore and the second bore open through the distal end of the shaft in rotationally spaced relationship to one another such that the light is positioned on the same side of the probe relative to the tip as the first endoscope.

7. The probe of claim 1, further comprising an elongate cylindrical sleeve enclosing the shaft.

8. The probe of claim 1, wherein the tip is detachably secured to the distal end of the shaft.

9. The probe of claim 8, wherein the tip being detachably secured to the distal end of the shaft enables the tip to be replaced without replacing the entire probe.

10. A probe, comprising:
an enlarged proximal end for cooperation with the hand of a surgeon using the probe to aid in controlling the probe;
an elongate shaft having a longitudinal axis and extending from the enlarged proximal end to a distal end;
a reduced diameter tip at the distal end of the shaft, the tip having a sharpened distal point having a hardness and configuration adapted to be pushed through a vertebral pedicle to form a hole for reception of a pedicle screw;
a first bore extending longitudinally through the shaft, and a first endoscope associated with the first bore, the first endoscope including a camera and placed within the first bore in the shaft rearward of the distal point of the tip and being connected with an endoscopic monitor to provide the surgeon with a first direct view of an area being treated;
a second bore extending longitudinally through the shaft, and a light associated with the second bore, the light including a fiber optic optical connector placed within the second bore in the shaft rearward of the distal point of the tip and being connected with a light source to illuminate the area being treated;
a third bore extending longitudinally through the shaft, and a second endoscope associated with the second bore, the second endoscope including a camera positioned at the distal end of the shaft and being connected with an endoscopic monitor to provide the surgeon with a second direct view of the area being treated;
a fourth bore extending longitudinally through the shaft, and a conduit extending through the fourth bore for conveying a fluid to the area being treated to flush away from the area being treated body fluid and debris that would otherwise obscure the area being treated; and
an elongate cylindrical sleeve enclosing the shaft.

11. A system for performing a surgical procedure in an area being treated, the system comprising:
an endoscopic monitor; and
a probe, the probe comprising:
an enlarged proximal end for cooperation with the hand of a surgeon using the probe to aid in controlling the probe;
an elongate shaft having a longitudinal axis and extending from the enlarged proximal end to a distal end;
a reduced diameter tip at the distal end of the shaft, the tip having a sharpened distal point having a hardness and configuration adapted to be pushed through a vertebral pedicle to form a hole for reception of a pedicle screw;
a first bore extending longitudinally through the shaft, and a first endoscope associated with the first bore, the first endoscope including a camera and placed within the first bore in the shaft rearward of the distal point of the tip and being connected with the endoscopic monitor to provide the surgeon with a first direct view of an area being treated; and
a second bore extending longitudinally through the shaft, and a light associated with the second bore, the light including an optical connector placed within the second bore in the shaft rearward of the distal point of the tip and being connected with a light source to illuminate the area being treated.

12. The system of claim 11, wherein the optical connector is fiber optic.

13. The system of claim 11, wherein the probe further includes a third bore extending longitudinally through the shaft, and a second endoscope associated with the second bore, the second endoscope including a camera positioned at the distal end of the shaft and being connected with an endoscopic monitor to provide the surgeon with a second direct view of the area being treated.

14. The system of claim 13, wherein the first endoscope and the second endoscope are connected with the endoscopic monitor.

15. The system of claim 11, wherein the probe further includes a fourth bore extending longitudinally through the shaft, and a conduit extending through the fourth bore for conveying a fluid to the area being treated to flush away from the area being treated body fluid and debris that would otherwise obscure the area being treated.

16. The system of claim 11, wherein the first bore and the second bore open through the distal end of the shaft in rotationally spaced relationship to one another such that the light is positioned on the same side of the probe relative to the tip as the first endoscope.

17. The system of claim 11, wherein the probe further comprises an elongate cylindrical sleeve enclosing the shaft.

18. The system of claim 11, wherein the tip is detachably secured to the distal end of the shaft.

19. The system of claim 18, wherein the tip being detachably secured to the distal end of the shaft enables the tip to be replaced without replacing the entire probe.

* * * * *